United States Patent [19]

Trick et al.

[11] Patent Number: 5,114,398

[45] Date of Patent: May 19, 1992

[54] FEMALE INCONTINENCE CONTROL DEVICE WITH MECHANICALLY OPERABLE VALVE

[75] Inventors: Robert E. Trick, Racine; Carl B. Barwick, Caledonia, both of Wis.

[73] Assignee: Medical Engineering Corporation, Racine, Wis.

[21] Appl. No.: 485,696

[22] Filed: Feb. 27, 1990

[51] Int. Cl.⁵ ............................................ A61M 25/00
[52] U.S. Cl. ............................. 600/29; 128/DIG. 25; 604/96; 604/249
[58] Field of Search ............... 600/29, 30, 31; 604/96, 604/99, 102, 249; 128/DIG. 25

[56] References Cited

U.S. PATENT DOCUMENTS

| | | | |
|---|---|---|---|
| 3,087,492 | 4/1963 | Gurth | 604/99 |
| 3,399,677 | 9/1968 | Gould et al. | 604/99 |
| 3,503,400 | 3/1970 | Osthagen et al. | 128/DIG. 25 |
| 3,642,004 | 2/1972 | Osthagen et al. | 128/DIG. 25 |
| 3,797,478 | 3/1974 | Walsh et al. | 600/29 |
| 4,026,298 | 5/1977 | Grausz | 604/249 |
| 4,198,984 | 4/1980 | Taylor | 604/99 |
| 4,553,959 | 11/1985 | Hickey et al. | 128/DIG. 25 |
| 4,579,554 | 4/1986 | Glassman | 604/96 |
| 4,813,935 | 3/1989 | Haber et al. | 604/99 |
| 4,932,938 | 6/1990 | Goldberg et al. | 604/96 |
| 4,946,449 | 8/1990 | Davis, Jr. | 128/DIG. 25 |

Primary Examiner—Stephen C. Pellegrino
Assistant Examiner—Ralph A. Lewis
Attorney, Agent, or Firm—Stuart E. Krieger

[57] ABSTRACT

The female incontinence control device includes a conduit having inlet and outlet openings for receiving, conducting and discharging urinary fluid. The device also includes stabilizing structure for holding the conduit in its installed position relative to the urethra and bladder such that a drainage inlet opening can receive fluid from the bladder, and the outlet discharge opening is positioned outside the urethra. The conduit includes a manually actuatable drainage control valve adapted to be positioned outside the urethra. Manual actuation of the valve from a closed position to an open position is thus easily accomplished by manipulating an actuator member at a distal end portion of the conduit to selectively control urinary discharge from the conduit. The actuator member can be formed as an extension of a valve member or interconnected with the valve member through a flexible connecting link. The actuator can also be constituted as a flexible discharge member which permits control of the direction of discharge or urinary fluid.

21 Claims, 5 Drawing Sheets

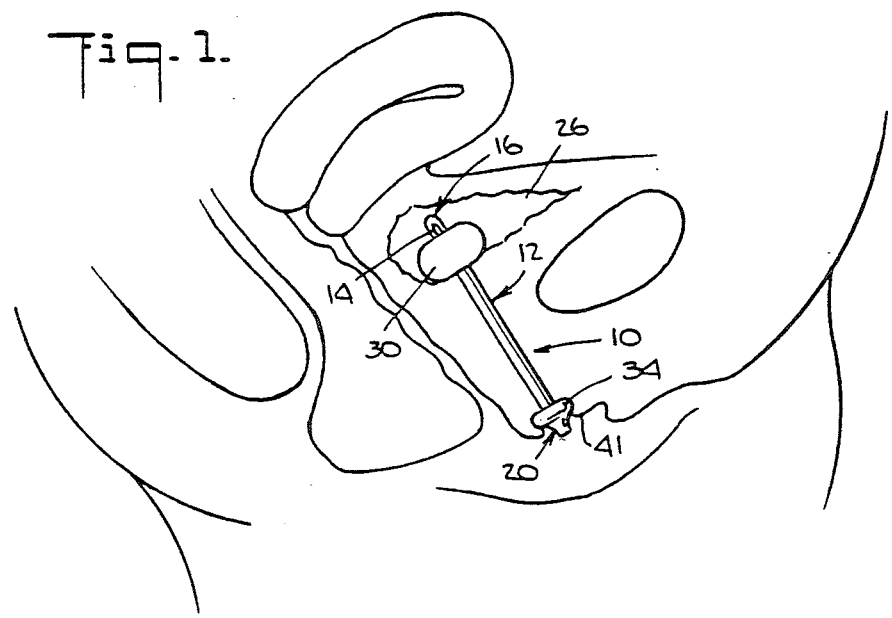
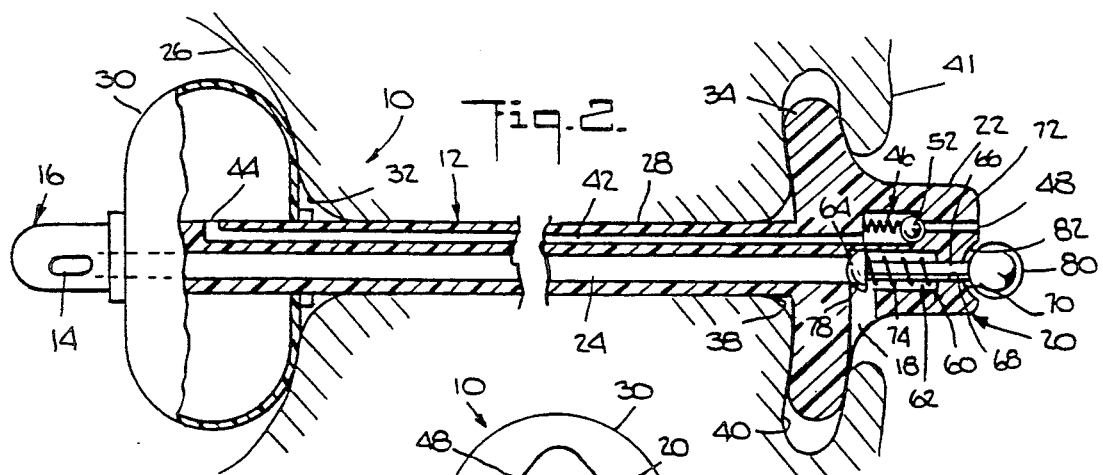
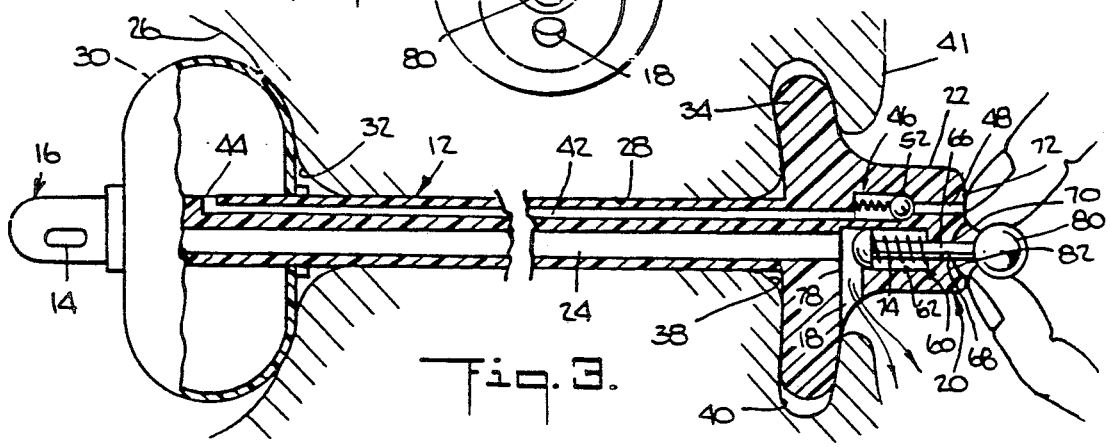

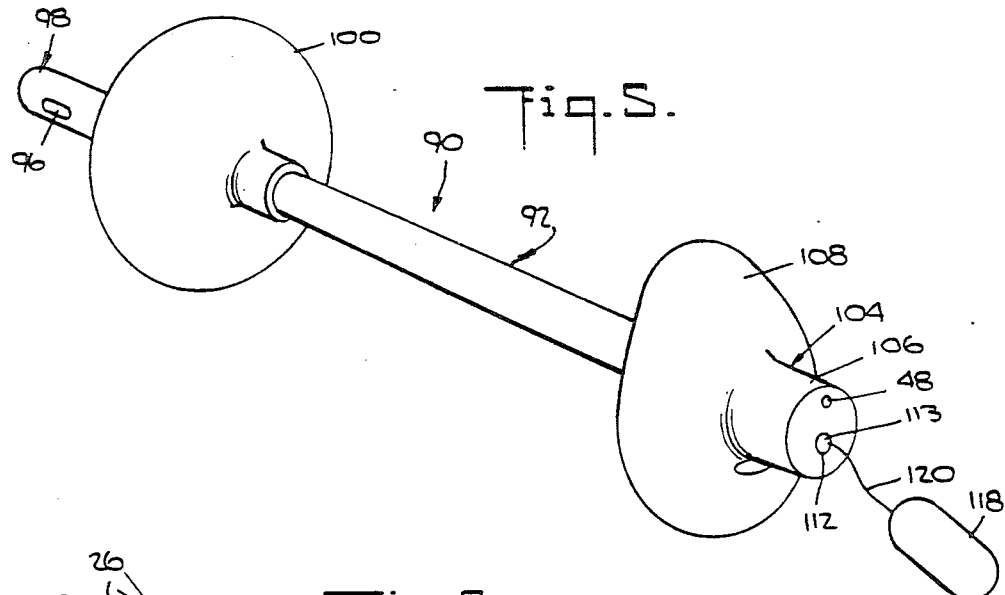
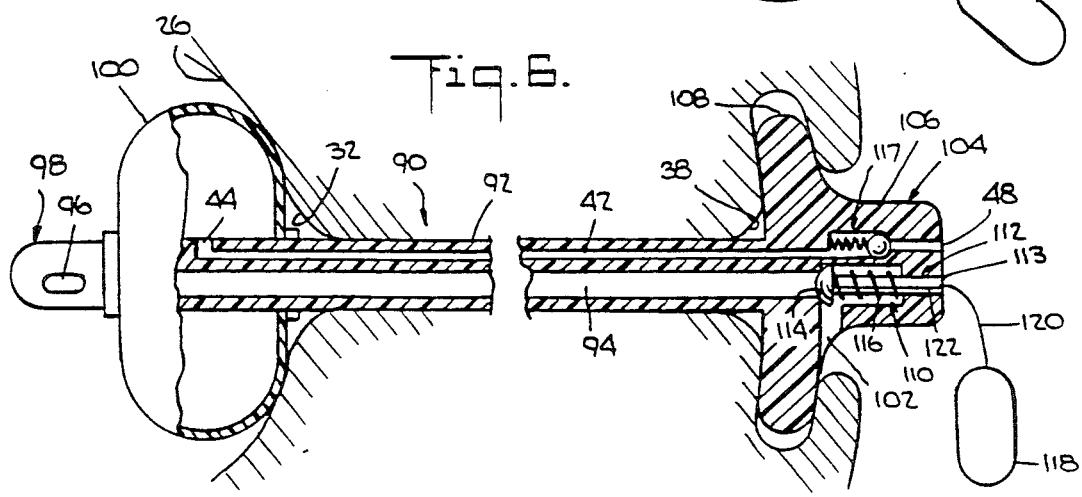
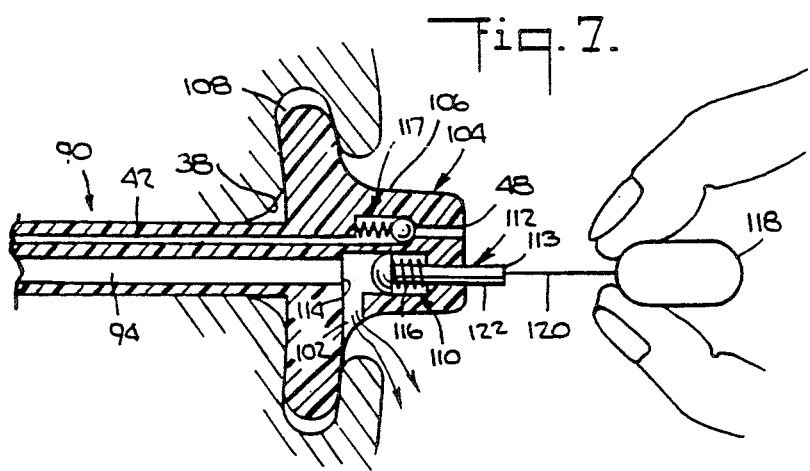

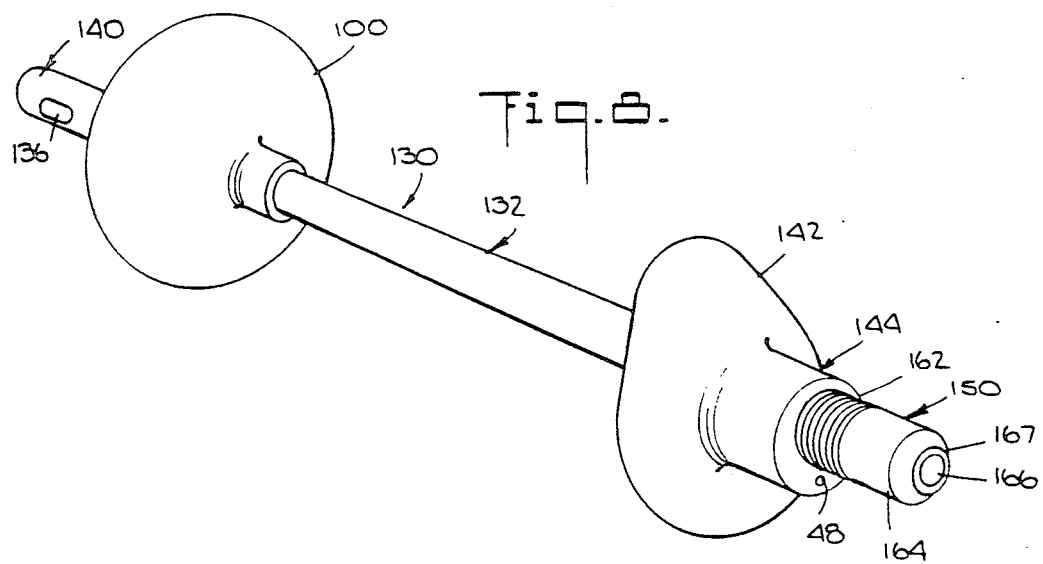
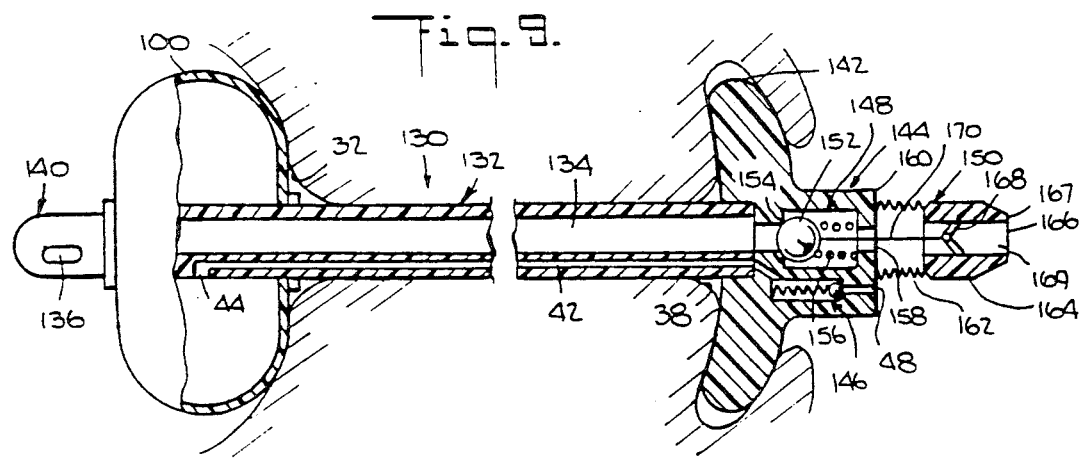
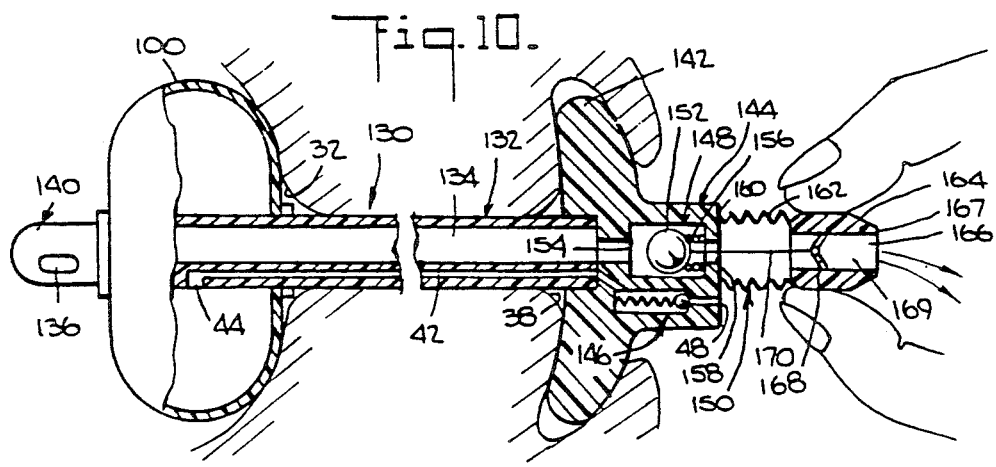

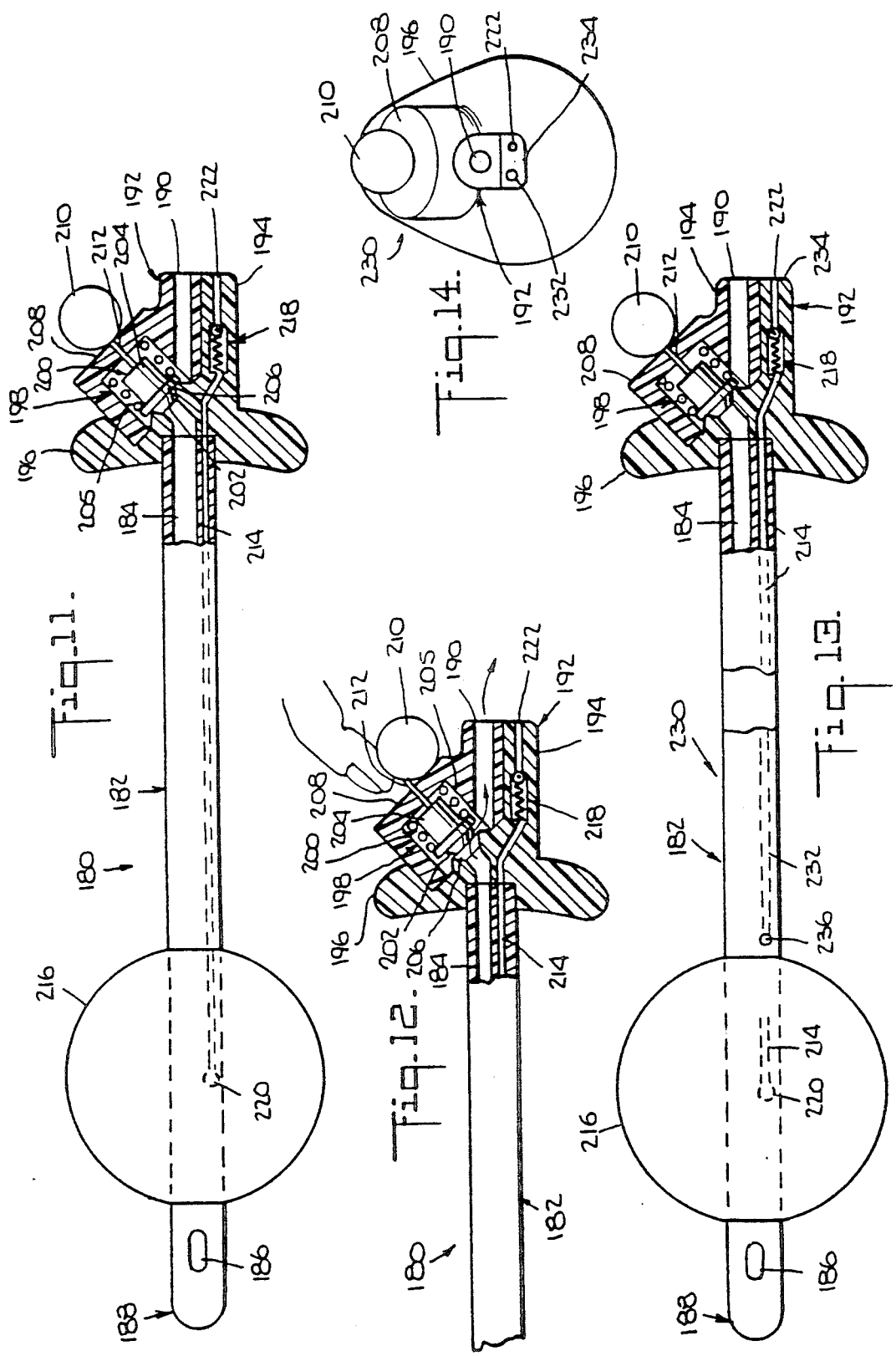

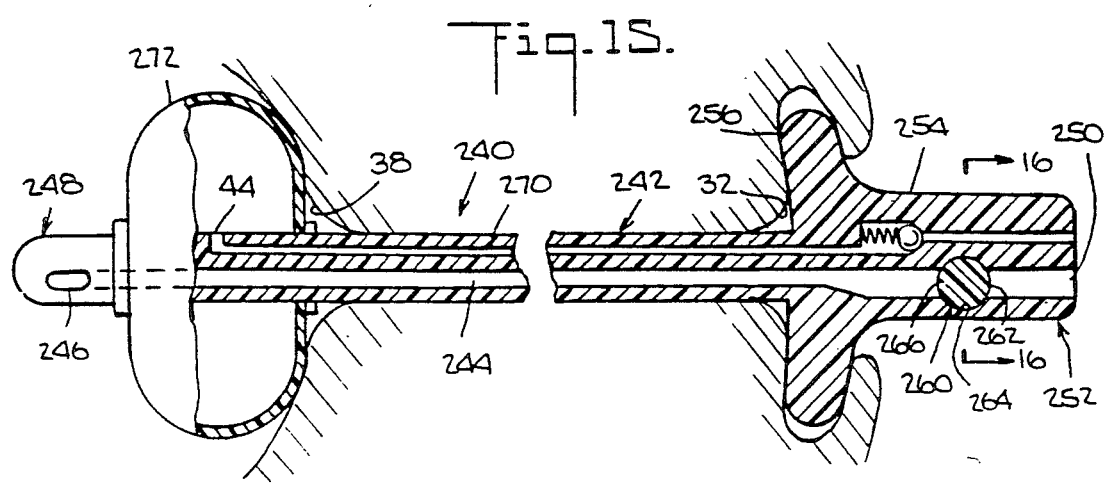
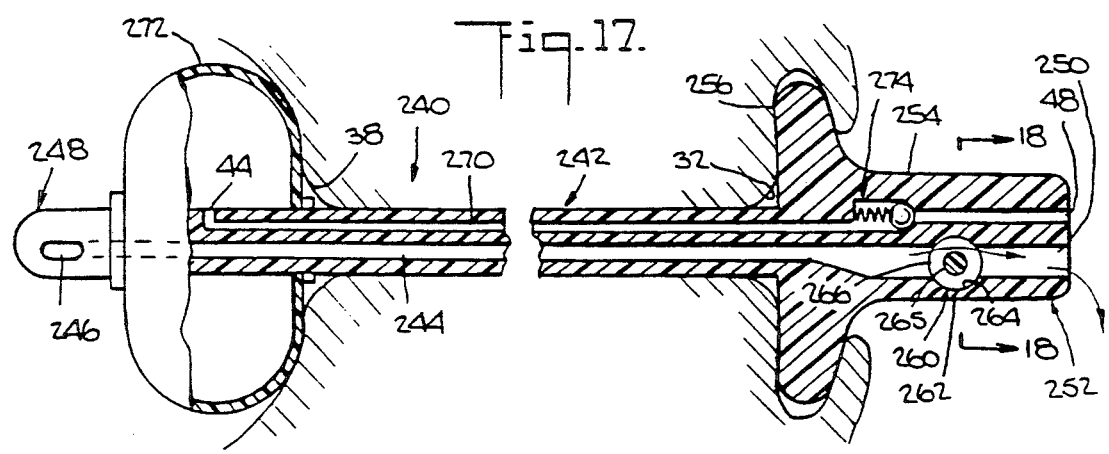
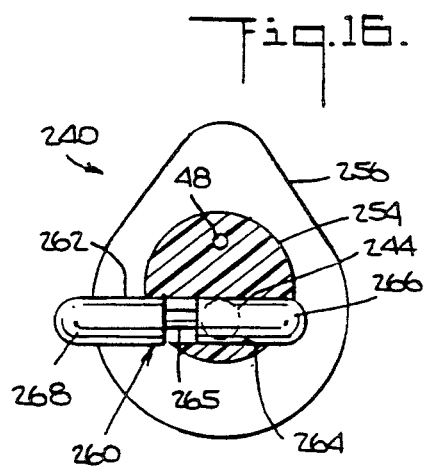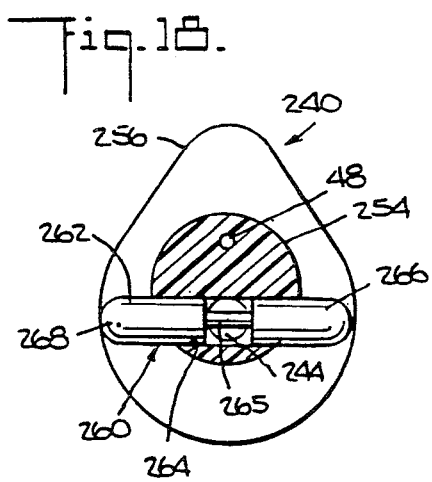

FEMALE INCONTINENCE CONTROL DEVICE WITH MECHANICALLY OPERABLE VALVE

BACKGROUND OF THE INVENTION

This invention relates to devices for controlling female incontinence and more particularly to a novel female incontinence control device that employs a manually actuatable valve for controlling urinary discharge.

Urinary incontinence in women is a common condition that can result from a variety of causes including illness, injury or debilitation. An incontinent condition is usually characterized by a weakness or total lack of functioning of the muscles that control expansion and contraction of the urinary sphincter. Thus far there are no known surgical procedures that satisfactorily correct an incontinent condition to the extent that bladder control is substantially restored.

Attempts to ameliorate the condition of incontinence include the use of passive devices such as a collection bag worn by the user to collect urine as it drains from the urethra. One drawback of this arrangement is that the bladder continuously drains into the collection bag without affording the user any control of urinary discharge. A further drawback of this arrangement is that the collection bag must accompany the user and thus inhibits the user's activities. Still another drawback is that the collection bag can provide a path for bacterial infection.

Absorbent pads similar to diapers are another example of a passive remedy for individuals having an incontinent condition. Absorbent pads have disadvantages similar to those described for the collection bag and also require frequent changing.

Other known devices which deal with the problem of female incontinence attempt some form of drainage control and include catheters, draining probes and dilators, such as shown in U.S. Pat. Nos. 4,194,508; 4,198,979 and 4,563,183. Generally such known devices also include an external fluid collection system fastened to a portion of the user's body.

In general, catheters, collection bags and absorbent pads are cumbersome and awkward to use in dealing with incontinence, and are often a source of embarrassment to the user.

Attempts to address such problems as lack of control, bulkiness, discomfort, embarrassment and inhibition of activities have led to the development of valved incontinence control devices, which eliminate the need for external collection systems and allow the user to exercise control over the discharge of urinary fluids from the urinary tract. Examples of such devices are shown in U.S. Pat. Nos. 3,503,400; 3,731,670; 3,939,821 and 4,024,855.

In U.S. Pat. No. 3,503,400, a manually controllable valve is positioned within the urethra near the bladder. Since the valve is intended to be recessed in the urethral passage near the bladder, it is necessary that the valve components be sufficiently small to function within the environment of the urethral passage. Due to the relatively small size of the valve in the urethral passage, the fluid flow rate through the device is relatively low requiring an extensive amount of time to empty the bladder. Such a time consuming process can be discomforting and inconvenient to the user.

Other known devices of the type shown in U.S. Pat. Nos. 3,939,821 and 4,024,855 require surgical implantation, and are essentially permanent installations. Should operational problems arise with these devices, further surgery may be required.

It is thus desirable to provide a female incontinence control device that is manually actuatable by the user to control urinary discharge, permits relatively quick emptying of the bladder, does not unduly impede normal activity of the user and does not require surgical installation.

OBJECTS AND SUMMARY OF THE INVENTION

Among the several objects of the invention may be noted the provision of a novel female incontinence control device having a manually actuatable control valve for controlling urinary discharge, a novel female incontinence control device which is substantially entirely contained within the urethral tract of the user, a novel female incontinence control device which does not require surgical implantation, a novel female incontinence control device having a control valve that can be operated by manual manipulation of an actuator member, a novel female incontinence control device which normally prevents urinary discharge to maintain continence and permits such discharge upon simple manipulation of a control valve, and a novel female incontinence control device having a control valve that is positioned outside the urinary opening and can thus be sized to provide a relatively high rate of fluid discharge.

Other objects and features of the invention will be in part apparent and in part pointed out hereinafter.

In accordance with the invention, the female incontinence control device includes a conduit having a proximal end with an inlet opening adapted to receive urinary fluids that drain from the bladder, and a distal end with an outlet opening through which urinary fluids are discharged.

A manually actuatable discharge control valve provided at the distal end of the conduit is adapted to be located outside the urethral opening. Under this arrangement, the valve can be sized to provide a comfortable discharge rate since it need not be recessed in the urethral canal. The control valve is thus manually accessible outside the urethra. The accessibility of the control valve for manual actuation does not inhibit or interfere with general physical activity of the user.

In several embodiments of the invention the valve member of the control valve is movable via an actuator device that is directly connected to the valve member or indirectly connected through a flexible connecting member.

In at least one embodiment of the invention the actuator member is actuatable using one finger.

In several embodiments of the invention the valve member is maintained in a normally closed position by a biasing spring when the incontinence control device is not being used for discharge purposes. As a safety factor, the biasing means can be selected to permit the valve to open at a predetermined pressure level that avoids the possibility of injury to the bladder or kidneys because of excessive pressure buildup in the bladder.

In another embodiment of the invention the control valve is manually manipulable into an open or a closed position.

All embodiments of the invention provide for location of the control valve in a central axial portion of the conduit, or at an offset with respect to the central axial portion by angles of from 45° to approximately 90°.

At least one embodiment of the female incontinence control device includes a flexible discharge member which is operable to direct the flow of discharged fluid in a predetermined direction. The flexible discharge member is extendible and, in the course of such extension, operates to actuate a valve member from a normally closed position into an open position A biasing spring in the valve is operable to restore the valve member to its normally closed position. The valve member is connected to the discharge member such that movement of the valve member to its normally closed position also serves to retract the discharge member to its nonextended position.

All embodiments of the invention can include a lumen for infusing antimicrobial agent into the urethra to avoid bacterial infection.

The invention accordingly comprises the constructions hereinafter described, the scope of the invention being indicated in the claims.

DESCRIPTION OF THE DRAWINGS

In the accompanying drawings,

FIG. 1 is a simplified schematic anatomical view showing the general location of an incontinence control device incorporating one embodiment of the invention;

FIG. 2 is an enlarged simplified schematic view thereof partly shown in section, with the valve means therein in a normally closed position;

FIG. 3 is a view similar to FIG. 2 showing the valve means in an open condition;

FIG. 4 is a distal end view thereof;

FIG. 5 is a simplified perspective view of another embodiment of the invention;

FIG. 6 is an enlarged simplified schematic view thereof, partly shown in section, with the valve means in a normally closed position;

FIG. 7 is a fragmentary view thereof, similar to FIG. 6, with the valve means in an open condition;

FIG. 8 is a simplified perspective view of still another embodiment of the invention;

FIG. 9 is an enlarged simplified schematic view thereof, partly shown in section, with the valve means in a normally closed position;

FIG. 10 is a view similar to FIG. 9 with the valve means in an open condition;

FIG. 11 is an enlarged simplified schematic view, partly shown in section, of a further embodiment of the invention wherein the valve means is in a normally closed position;

FIG. 12 is a fragmentary detail view thereof showing the valve means in an open condition;

FIG. 13 is an enlarged simplified schematic view partly shown in section, of a still further embodiment of the invention wherein the valve means is in a normally closed position;

FIG. 14 is a distal end view thereof;

FIG. 15 is an enlarged simplified schematic view partly shown in section of still another embodiment of the invention wherein the valve means is in a closed position;

FIG. 16 is a sectional view taken on the line 16—16 of FIG. 15;

FIG. 17 is a view similar to FIG. 15 wherein the valve means is shown in an open condition; and FIG. 18 is a sectional view taken on the line 18—18 of FIG. 17.

Corresponding reference characters indicate corresponding parts throughout the several views of the drawings.

DETAILED DESCRIPTION OF THE INVENTION

A female incontinence control device incorporating one embodiment of the invention is generally indicated by the reference number 10 in FIGS. 1-4.

The device 10 includes a conduit 12 having an inlet opening 14 at a proximal end portion 16 and an outlet opening 18 at a distal end portion 20. The conduit 12, which can be formed of any suitable biocompatible material such as silicone, also includes an enlarged distal section 22 at the distal end portion 20. The inlet and outlet openings 14 and 18 communicate through a lumen 24 formed within the conduit 12. The lumen 24 constitutes a drainage passage for urine from the bladder 26 of a user to the outlet opening 18 of the conduit 12.

To maintain stability of the conduit 12 in its installed position in the urethra 28 and to prevent migration of the conduit 12 relative to the urethra 28, anchoring structures larger than the diameter of the urethra are provided at the proximal and distal end portions 16 and 20 of the conduit 12. For example, a bladder engaging member such as a conventional inflatable bladder balloon 30 is provided on the conduit 12 distally of the inlet opening 14 for location at a neck portion 32 of the bladder 26. The balloon 30 helps to anchor the device 10 by preventing antegrade movement. In addition, an oval or egg-shaped flange 34 is provided at the enlarged distal section 22 of the conduit 12 at the distal end portion 20. The flange 34 is adapted to be positioned outside the urethral orifice 38 to bear against the meatus 40 inwardly of the labia 41. The flange 34 is sized and shaped to prevent retrograde movement of the conduit 12 into the bladder 26. If desired, the flange 34 can be formed in other suitable shapes that will prevent such retrograde movement.

Although the anchoring structure of the device 10 is represented by the inflatable bladder balloon 30 and the flange 34, it will be apparent to those skilled in the art that other suitable known anchoring structures can be employed, such as, for example, non-inflatable collapsible bulges, Malecot tips and spirals.

The bladder balloon 30 is inflated through a lumen 42 having a proximal end 44 that opens into the interior of the balloon 30. The inflation lumen 42 does not communicate with the drainage lumen 24.

An inflation check valve generally indicated at 46 is provided at the enlarged distal section 22 in alignment with the inflation lumen 42. The valve 46 is accessed at a distal end 48 of the inflation lumen 42. Inflation fluid (not shown) is thus introduced into the bladder balloon 30 through the check valve 46 by inserting a known inflation device such as an inflation syringe (not shown) into the distal end 48. The inflation syringe infuses fluid past a spring biased ball check 52 to inflate the bladder balloon 30.

Referring to FIGS. 2 and 3, a manually actuatable valve generally indicated at 60 is provided at the distal end portion 20 of the conduit 12, distally of the flange 34 in the enlarged distal section 22 for location outside the urethral opening 38.

The valve 60 includes a movable valve member 62 having a generally hemispherical valve head 64 joined to a valve stem 66. The valve head 64 and the valve stem 66 can be formed of a suitable material such as stainless steel. Alternatively, the valve head 64 can be formed of silicone with the valve stem 66 formed of stainless steel.

The valve stem 66 is slidably movable in a valve stem passage 68 which has an open end 70 at an end surface 72 of the enlarged distal section 22. The valve member 62 is biased by a biasing spring 74 to a normally closed position wherein the valve head 64 engages a valve seat 78.

An actuation member 80 disposed outside the valve stem passage 68 is joined to the valve stem 66. The actuation member 80 can be of spherical or cylindrical shape, for example, and is normally received in a complementary shaped recess 82 formed in the end surface 72.

In using the incontinence control device 10, the conduit 12 with the bladder balloon 30 in a deflated condition is inserted into the urethra 28, pursuant to conventional procedures such as used for example, in installing a Foley catheter. After the conduit 12 is inserted into the urethra 28 up to the flange 34, a suitable known syringe or inflation connector (not shown) may be used to inject inflation fluid directly into the inflation lumen 42, via the access passage 50 and valve 46 to inflate the bladder balloon 30, whereby the conduit 12 is held in the position shown in FIG. 1.

When the valve 60 is in a normally closed position as shown in FIG. 2, urine flow through the drainage lumen 24 is blocked such that urine accumulates in the bladder 26. The normally closed position of the valve 60 thus maintains continence for the user.

When bladder discharge is desired, the user manipulates the actuating member 80 away from the end surface 72 by gently pulling the actuating member 80 as shown in FIG. 3. Movement of the actuating member 80 causes the valve member 62 to displace away from the valve seat 78 into an open position against the force of the biasing spring 74. The valve member 62 will remain in the open position corresponding to the open condition of the valve 60 as long as the actuating member 80 is held away from the recess 82.

With the valve 60 in the open condition fluid can flow from the bladder through the drainage lumen 24 for discharge from the outlet opening 18. The bladder discharge can be easily and conveniently directed into a toilet in the same manner that such discharge is accomplished by individuals who do not require an incontinence device.

After bladder discharge is completed the user can release the actuating member 80 thereby allowing the valve member 62 to return to its normally closed position under the influence of the biasing spring 74.

The device 10 thus restores continence and allows the user to exercise control of bladder discharge without impediment and without the need for external collection devices.

Nonsurgical removal of the device 10 is easily accomplished by inserting a suitable deflator device, such as a deflation needle (not shown), sized to fit into the inflation valve access passage 50 at the enlarged distal section 22. The deflation needle is urged against the ball check 52 of the inflation valve 46 to open the valve 46. Fluid is thus drawn or permitted to drain from the bladder balloon 30 through the inflation lumen 42, past the inflation valve 46 into the deflator needle.

As another alternative for removing the device 10 from the urethra 28, should such removal be desired,
the distal end 20 of the conduit 12 at the enlarged distal section 22 can be cut with a suitable device such as a scissor at a point upstream of the inflation valve 46. The inflation lumen 42 can thus be bled to accomplish deflation of the bladder balloon 30. Once the bladder balloon 30 is deflated, the conduit 12 can be easily withdrawn from the urethra 26 and discarded.

If desired, the device 10 can be incorporated with a closed inflation system (not shown), wherein the bladder balloon 30 communicates with an inflation reservoir balloon (not shown). The reservoir balloon is connected to the inflation passage 42 for communication with the check valve 46. The inflation reservoir eliminates the need for a syringe or inflation connector. Pressure on the reservoir balloon after installing the device 10 in the urethra 28 causes the check valve 46 in the inflation lumen 42 to open, allowing the bladder balloon 30 to inflate. The inflation reservoir can be removed after installation of the device 10 is completed. In this variation of the device 10, removal is also accomplished in the same manner as previously described, as by using the deflation needle (not shown), or a scissor proximally of the check valve 46 to cut through the inflation lumen 42.

Another embodiment of the female incontinence control device is generally indicated by the reference number 90 in FIGS. 5-7. The device 90 includes a conduit 92 similar to the conduit 12 and includes a drainage lumen 94, an inlet opening 96 at a proximal end 98, with a bladder balloon 100. An outlet opening 102 is at a distal end 104 which also includes an enlarged distal section 106 with a flange 108 similar in shape to the flange 34 of the device 10.

A manually actuatable valve 110 similar to the valve 60 is at the distal end 104 to control discharge of fluid through the outlet opening 102.

The valve 110 includes a valve member 112 held in a normally closed position against a valve seat 114 by a biasing spring 116. The conduit 92 also includes an inflation check valve 117 similar to the inflation check valve 46 of the device 10.

An actuating member 118 is joined to the valve member 112 via a flexible connecting link 120. The actuating member 118 is preferably formed of silicone and can be of any suitable shape such as cylindrical with rounded end portions to facilitate manipulation. The flexible connecting link 120 can be formed of a suture material such as braided Dacron, for example.

The flexible connecting link 120 can be secured to the actuating member 118 by, for example, passing one end of the link 120 through the actuating member 118 and knotting the end (not shown) to prevent the link 120 from becoming free of the actuating member 118.

An opposite end of the connecting link 120 can be passed through an end portion 113 of the valve member 112 and similarly knotted. For example, the generally cylindrical valve stem 122 of the valve member 112 can be formed with a flat portion (not shown) to accommodate the knotted end of the link 120 and allow sufficient clearance between the knotted end of the link 120 and the biasing spring 116. The flat portion of the valve stem would be foreshortened so as not to extend past the spring 116 when the spring is compressed as shown in FIG. 7.

The device 90 is installed in the urethra 26 in the manner similar to that described for the device 10. In using the device 90, the actuating member 118 is gently pulled away from the distal end 104 of the conduit 92.

The actuating member 118 thus overcomes the force of the biasing spring 116 and moves the valve member 112 away from the valve seat 114 to place the valve 110 in an open condition. The valve 110 remains in the open condition as long as the actuating member 118 is held away from the distal end 104 of the conduit 92 as shown in FIG. 7, thus overcoming the biasing force of the biasing spring 116. Operation and use of the device 90 is otherwise similar to operation and use of the device 10.

Still another embodiment of the female incontinence control device is generally indicated by the reference number 130 in FIGS. 8-10. The incontinence control device 130 includes a conduit 132 having a drainage lumen 134 with an inlet opening 136 and a bladder balloon 138 at a proximal end portion 140. A flange 142 similar in shape to the flange 108 is provided at a distal end portion 144 of the conduit 132. An inflation check valve 146 similar to the inflation check valve 46 is provided at the distal end 144.

The conduit 132 also includes a drainage control valve 148 and a discharge member 150 joined to the distal end 144 in any suitable known manner, as for example, by bonding or integral molding with the conduit 132.

The valve 148 includes a ball check 152 which is held in a normally closed position against a valve seat 154 by a biasing spring 156. The ball check 152 can be formed of silicone or any other suitable material. An opening 158 is formed in a distal end wall 160 of the conduit 132 opposite the valve seat 154.

The discharge member 150 includes a flexible extendible bellows portion 162 joined to a relatively inflexible collar portion 164. An outlet or discharge opening 166 is provided at a free end 167 of the collar 164. The collar 164 is connected to the ball check 152 via an anchor piece 168 that extends across an inner hollow section 169 of the collar 164. A flexible connecting link 170, similar to the flexible connecting link 120, is connected at one end to the anchor piece 168 and at an opposite end to the ball check 152.

The flexible connecting link 170 can be secured to the ball check 152 by passing the link through the ball check and knotting the end of the link in a manner similar to that described for securing the connecting link 120 to the actuating member 118. An opposite end of the link 170 can be knotted or otherwise secured to the anchor piece 168.

The conduit member 132, the flange 142, the bellows 162 and the collar 164 can be formed as separate members or molded integrally from a suitable elastomeric material such as silicone.

The incontinence device 130 is installed in a manner similar to that previously described for the device 10. In using the incontinence device 130, the valve 148 is maintained in a normally closed position by the force of the biasing spring 156 against the ball check 152. In this manner the bladder is permitted to accumulate fluid.

When discharge of bladder fluid is desired, the collar portion 164 is gently manipulated away from the distal end wall 160 of the conduit 132. The force applied to the collar 164 is transmitted through the connecting link 170 to the ball check 152 to move the ball check 152 away from the valve seat 154. The valve 148 is thus placed in an open condition to permit accumulated fluid in the bladder to flow through the drainage lumen 134 past the valve seat 154 for discharge through the discharge opening 166 of the discharge member 150.

The flexible, extendable features of the discharge member 150 permit the collar to be oriented in any selected direction relative to the direction of flow of fluid through the drainage lumen 134. Thus the device 130 is ideal for use by individuals who, because of illness or infirmity, cannot use a conventional toilet facility and must resort to using a bed pan, a basin or other outside vessel.

When discharge is completed, the discharge member 150 is manipulated to permit retraction toward the distal end wall 160 under the influence of the biasing spring 156. The biasing spring 156 also urges the ball check 152 against the valve seat 154 to automatically restore the valve 148 to its normally closed position wherein bladder discharge is prevented. The valve 130 thus maintains continence of an otherwise incontinent individual.

A further embodiment of the female incontinence control device is generally indicated by the reference number 180 in FIGS. 11-12.

The device 180 includes a conduit 182 having a drainage lumen 184 with an inlet opening 186 at a proximal end 188, and an outlet opening 190 at a distal end portion 192. The distal end portion 192 of the conduit 182 includes an enlarged distal section 194 and a flange 196 similar in shape to the flange 108.

A valve 198 is provided between the enlarged distal section 194 and the flange 196 for location outside the urethral opening. The valve 198 includes a valve member 200 having a poppet head 202, and a stem portion 204 formed of a suitable material such as stainless steel. The valve 198 further includes a biasing spring 205 that normally biases the poppet head 202 against a valve seat 206. The valve 198 also includes an end wall surface 208 that is inclined relative to the drainage lumen 184 by an angle of approximately 30-45°, the valve member 200 being inclined approximately 45-60° to the main section of the drainage lumen 184.

A spherical shaped actuation member 210 disposed outside the inclined end wall 208 is connected to the valve member 200 via a flexible connecting link 212 similar to the flexible connecting link 120. The actuation member 210 can be formed of any suitable material such as silicone. The connecting link 212 is secured to the actuation member 210 by passing one end of the link 212 through the actuation member 210 and knotting said end in the manner previously described for securing the connecting link 12 to the actuation member 118 of the device 90.

The opposite end of the connecting link 212 is secured to the stem portion 204 of the valve member 200 in a manner similar to that previously described for securing the connecting link 120 to the valve stem 122 of the device 90.

The connecting link 212 is of a predetermined length that permits engagement of the actuating member 210 against the inclined end wall 208 when the valve 198 is in a normally closed position. However the connecting link 212 is always relatively slack, even when the valve 198 is in its normally closed condition. The slackness assures that engagement of the actuating member 210 against the inclined end wall 208 does not prevent the valve member 200 from remaining in its normally closed position under the influence of the biasing spring 205 when there is no actuation force applied to the actuation member 210.

The device 180 further includes an inflation lumen 214 for inflating a bladder balloon 216 through a check valve 218 similar to the check valve 46 of the device 10.

The inflation lumen 214 includes an outlet end 220 that communicates with the interior of the bladder balloon 216 and an inlet end 222 in an arrangement similar to that of the previously described embodiments.

The device 180 is installed in a manner similar to that previously described for the device 10. In using the device 180, the actuating member 210 is in a rest position as shown in FIG. 11 when the valve member 200 is in its normally closed position. When urinary discharge is desired the actuating member 210 can be displaced along the inclined end wall 208 away from the rest position of FIG. 11 using one finger as shown in FIG. 12. Movement of the actuating member 210 away from the rest position causes the valve member 200 to move away from the valve seat 206 into an open position against the force of the biasing spring 205.

The valve member 200 will remain in the open position corresponding to the open condition of the valve 190 as long as the actuating member 210 is maintained away from the rest position of FIG. 11. Alternatively, the actuating member 210 can be gently pulled in a manner similar to that described for operating the actuating member 118 of the device 90.

With the valve 198 in the open condition, fluid can flow from the bladder through the drainage lumen 184 for discharge from the outlet opening 190. Manipulation of the actuating member 210 back to the rest position allows the valve member 200 to return to its normally closed position under the influence of the biasing spring 205.

It will be noted that since the valve member 200 is offset from the longitudinal axis of the drainage lumen 184 and spaced from the outlet opening 190, the enlarged distal section 194 can be of a relatively smaller size than the enlarged distal sections 22 and 106 of the devices 10 and 90.

A further embodiment of the female incontinence control device is generally indicated by the reference number 230 in FIGS. 13 and 14. The device 230 is a variation of the device 180, by provision of a lumen 232 for infusing antimicrobial agents into the urethra. The device 230 is otherwise identical to the device 180.

The antimicrobial infusion lumen 232 is accessible at an end surface 234 of the enlarged section 194 and includes a proximal open end 236 in the wall of the conduit 182. The opening 236 is at a predetermined distance from the flange 196 to ensure that such opening is in the urethral passage, preferably toward the proximal end portion of said passage.

The lumen 234 for infusion of antimicrobial agents is accessed in the same manner as the inflation lumen 232 and is used for flushing an antimicrobial agent into the urethra to guard against infection of the urethra.

Another embodiment of the female incontinence control device is generally indicated by the reference number 240 in FIG. 15. The device 240 includes a conduit 242 having a drainage lumen 244 with an inlet opening 246 at a proximal end portion 248, and an outlet opening 250 at a distal end portion 252. The distal end portion 252 of the conduit 242 includes an enlarged distal section 254 and a flange 256 similar in shape to the flange 108.

A drainage control valve 260 is provided in the enlarged distal section 254 intermediate the flange 256 and the outlet opening 250 in alignment with the drainage lumen 244.

The valve 260 includes a slidable valve member 262 constrained to slide transversely of the enlarged distal section 254 in a complementary shaped transverse passage 264. The valve member 262, which can be formed of stainless steel or a rigid biocompatible plastic such as polycarbonate or polysulfone, includes a stem 265 with enlarged capsule-shaped end portions 266 and 268.

The capsule-shaped end portions 266 and 268 have a predetermined snug fit in the transverse passage 264 such that the valve member 262 is slidably movable in the transverse passage 264 yet can remain detented wherever it is moved because of such predetermined snug fit.

The capsule-shaped end portions 266 and 268 project transversely from the enlarged distal section 262 and thus constitute actuators that are manually accessible for actuating the valve member 262 to a desired position.

The device 240 also includes an inflation lumen 270 for inflating a bladder balloon 272 through a check valve 274 similar to the check valve 46 of the device 10. The device 240 is installed in a manner similar to that previously described for the device 10.

In using the device 240, the valve 260 can be maintained in a closed position when either one of the end portions such as 266 is recessed in the passage 264 and the opposite non-recessed end portion such as 268 projects from the enlarged distal section 254 in the manner shown in FIG. 16. Under this arrangement, the enlarged end portion 266 blocks the drainage lumen 244, as shown in FIG. 15, to prevent fluid from flowing through the conduit 182. Fluid thus accumulates in the bladder.

When bladder discharge is desired, the projecting end portion 268 is manually pushed toward the enlarged distal section 254 until both of the enlarged end portions 266 and 268 project substantially equal amounts from the enlarged distal section 254 as shown in FIG. 18. It will be noted that the stem portion 265, which is diametrically reduced relative to the enlarged end portions 266 and 268, registers with the drainage lumen 244 but does not obstruct passage of fluid through the drainage lumen.

It should also be noted that bladder discharge can occur even when the enlarged end portions 266 and 268 do not project exactly equal amounts from the enlarged distal section 254. Thus there is no need for a fine degree of accuracy in ascertaining that the enlarged portions 266 and 268 project substantially equal amounts from the enlarged distal section 254. Generally the user can detect from the flow rate of bladder discharge the position of the enlarged end portions 266 and 268 that provide the maximum discharge rate.

When discharge is completed, the user can push either end portion, such as the end portion 266, toward the enlarged distal section 254 to a predetermined stop position wherein the end portion 266 blocks the drainage lumen 244 to prevent fluid discharge. Although not shown, any suitable known stop arrangement can be provided in the valve 260 for providing a predetermined stop position for each of the end portions 266 or 268 when either end portion is urged toward the enlarged distal section 254.

As will be apparent to those skilled in the art, suitable gasketing or other known sealing arrangements can be provided for the respective valve arrangements of the embodiments described herein and for the connecting links, where such links pass in and out of a valve chamber, to prevent unintended or undesired leakage of fluid through the valve or conduit structure.

In addition, the lumen for infusing antimicrobial agent can be incorporated in any of the described embodiments.

Some advantages of the present invention evident from the foregoing description include a manually actuatable female incontinence control device that is operable by a user through simple manipulation of a valve member that can be positioned outside the urethral opening. The incontinence control device does not require any external collection system and does not require surgical implantation or a complex actuation arrangement. The novel arrangement of the control valve at the distal end portion of the drainage conduit permits easy access to the valve for manipulation by a user.

A further advantage of the present invention is that a higher discharge rate can be obtained from the valve structure that is positionable outside the urethra rather than being recessed within the urethra.

In view of the above, it will be seen that the several objects of the invention are achieved and other advantageous results attained.

As various changes can be made in the above constructions without departing from the scope of the invention, it is intended that all matter contained in the above description or shown in the accompanying drawings shall be interpreted as illustrative and not in a limiting sense.

What is claimed is:

1. An incontinence device for a female, comprising:
   conduit means for receiving, conducting and discharging urinary fluids from the bladder, said conduit means having a proximal end portion with an inlet opening and a distal end portion with an outlet opening,
   an antegrade restraining member attached to said conduit means and positionable within the body for restraining said conduit means from moving antegrade within the urethra,
   a retrograde restraining member attached to said conduit means and positionable outside the urethra for restraining said conduit means from moving retrograde within the urethra, said retrograde and antegrade restraining means cooperably holding said conduit means in a predetermined position relative to the urethra so that said inlet opening receives urinary fluid from the bladder and said outlet opening is positioned outside the urethra, and
   mechanically actuatable valve means attached to the distal end portion of said conduit means for selectively controlling the flow of urinary fluid through said conduit means for discharge through said outlet opening, said valve means including a valve member within said retrograde restraining member, said valve member being outside the urethra when said conduit means is in said predetermined position, said valve member being manually actuatable between a normally closed position and an open condition, said open condition permitting flow of urinary fluid through said conduit means for discharge through said outlet opening, said valve means further including a biasing spring at said distal end portion for urging said valve member into said normally closed position.

2. The incontinence device as claimed in claim 1 wherein said valve member includes an actuating member, said actuating member being joined to said valve member.

3. The incontinence device as claimed in claim 1 wherein said valve member includes a valve stem movable relative to the proximal end portion of said conduit means when said valve member is placed in said open condition.

4. The incontinence device as claimed in claim 3 wherein said actuating member is joined to said valve stem.

5. The incontinence device as claimed in claim 4 wherein said valve stem is projectible from the proximal end portion of said conduit member when said valve means is placed in said open condition.

6. The incontinence device as claimed in claim 4 including a flexible connecting member joining said actuating member to said valve stem.

7. The incontinence device as claimed in claim 4 wherein said actuating member is inflexible and is integrally joined to said valve stem.

8. The incontinence device as claimed in claim 1 wherein said conduit means include a conduit member, and a flexible discharge member including said discharge opening is provided at the distal end portion of said conduit means to form an extension of said conduit member.

9. The incontinence device as claimed in claim 8 wherein said discharge member includes a bellows portion to permit expansion and contraction of said discharge member.

10. The incontinence device as claimed in claim 8 wherein said conduit member includes a drainage lumen and said discharge member is communicable with said drainage lumen through said valve means and the flexibility of said discharge member permits movement thereof in a selected direction to control the direction of orientation of said outlet opening and thereby control the direction of fluid discharge from said outlet opening.

11. The incontinence device as claimed in claim 8 wherein said discharge member is joined to said valve means and is extendible a predetermined amount away from said valve means such that the extension of said discharge member said predetermined amount causes said valve member to move from said closed position to said open condition.

12. The incontinence device as claimed in claim 11 wherein said discharge member includes an expandible and contractible bellows portion to permit extension of said discharge member said predetermined amount.

13. The incontinence device as claimed in claim 11 including a connecting member connecting said discharge member to said valve means such that extension of said discharge member said predetermined amount causes said connecting member to move said valve member from said closed position to said open condition.

14. The incontinence device as claimed in claim 1 including a drainage passage between said inlet opening and said outlet opening and wherein the direction of said drainage passage is substantially in a first direction and the direction of movement of said valve member between said closed position and said open condition is substantially in a second direction.

15. The incontinence device as claimed in claim 14 wherein the first and second directions are substantially parallel.

16. The incontinence device as claimed in claim 14 wherein the second direction is offset from the first direction by a predetermined angle of 60 degrees or less.

17. The incontinence device as claimed in claim 14 wherein the second direction is offset from the first direction by a predetermined angle of approximately 90 degrees.

18. The incontinence device as claimed in claim 17 wherein said conduit means includes a conduit member having an axis in said first direction and said valve member is slidable having opposite ends and being movable in said second direction, one of said valve member ends projecting from said conduit member when said valve member is in one of said open condition and closed position, said valve member being movable in said predetermined second direction to the other of said open condition and closed position when said one end of said valve member is displaced toward said conduit member.

19. The incontinence device as claimed in claim 18 wherein said valve member includes a reduced section that aligns with said fluid drainage passage when said valve member is moved to said open condition.

20. The incontinence device as claimed in claim 18 wherein said valve member includes an enlarged section that aligns with said fluid drainage passage to close said fluid drainage passage when said valve member is moved to said closed position.

21. The incontinence device as claimed in claim 1 wherein said conduit means includes a lumen having an inlet opening at said distal end portion and an outlet opening a predetermined distance from said proximal end portion to communicate with said urethra to permit infusion of an antimicrobial agent through said lumen into said urethra.

* * * * *